(12) United States Patent
Nir et al.

(10) Patent No.: US 8,481,572 B2
(45) Date of Patent: Jul. 9, 2013

(54) PHARMACEUTICAL COMPOSITIONS AND METHODS FOR THE TREATMENT OF CANCER

(75) Inventors: Uri Nir, Moshav Gamzo (IL); Sally Shpungin, Ramat-Gan (IL); Etai Yaffe, Oranit (IL); Moshe Cohen, Raanana (IL)

(73) Assignee: Urifer Ltd., Raanana (IL)

( * ) Notice: Subject to any disclaimer, the term of this patent is extended or adjusted under 35 U.S.C. 154(b) by 472 days.

(21) Appl. No.: 12/672,157

(22) PCT Filed: Aug. 10, 2008

(86) PCT No.: PCT/IL2008/001099
§ 371 (c)(1),
(2), (4) Date: Dec. 21, 2010

(87) PCT Pub. No.: WO2009/019708
PCT Pub. Date: Feb. 12, 2009

(65) Prior Publication Data
US 2011/0086861 A1    Apr. 14, 2011

Related U.S. Application Data

(60) Provisional application No. 60/935,364, filed on Aug. 9, 2007, provisional application No. 61/006,455, filed on Jan. 15, 2008.

(51) Int. Cl.
| | | |
|---|---|---|
| A61K 31/407 | (2006.01) | |
| A61K 31/415 | (2006.01) | |
| A61K 31/433 | (2006.01) | |
| A61K 31/496 | (2006.01) | |
| A61K 31/381 | (2006.01) | |
| A61K 31/4162 | (2006.01) | |
| A61K 31/429 | (2006.01) | |
| A61P 35/00 | (2006.01) | |

(52) U.S. Cl.
USPC ........... 514/363; 514/301; 514/279; 514/284; 514/285; 514/322; 514/324; 514/326; 514/342

(58) Field of Classification Search
USPC ................ 514/279, 284, 285, 301, 322, 324, 514/326, 342, 363
See application file for complete search history.

(56) References Cited

FOREIGN PATENT DOCUMENTS

| EP | 1547996 A1 | 6/2005 |
|---|---|---|
| JP | 11-116481 A | 4/1999 |
| WO | 02/066478 A1 | 8/2002 |
| WO | 02/092086 A1 | 11/2002 |
| WO | 03/017817 A2 | 3/2003 |
| WO | 2004/111061 A1 | 12/2004 |
| WO | 2006/101455 A1 | 9/2006 |
| WO | 2007/072093 A1 | 6/2007 |

OTHER PUBLICATIONS

Allard, P. et al., "Links Between Fer Tyrosine Kinase Expression Levels and Prostate Cell Proliferation", Molecular and Cellular Endocrinology, 2000, pp. 63-77, vol. 159.
Andreani, A. et al., "6-Thienyl and 6-phenylimidazo[2,1-b]thiazoles as Inhibitors of Mitochondrial NADH dehydrogenase", Eur. J. Med. Chem., Feb. 10, 1999, pp. 883-889, vol. 34.
Barlin, G..B. et al.,"Imidazo[1,2-b]pyridazines. XXI* Syntheses of Some 3-Acylaminomethyl-6-(chloro and iodo)-2-(substituted phenyl)-imidazo[1,2-b]pyridazines and -imidazo[1,2-a]pyridines and Their Interaction with Central and Mitochondrial Benzodiazepine Receptors", Part XX, Aust. J. Chem., Jul. 24, 1996, p. 451-457, , vol. 49.
Berridge, M.V. et al.,"Tetrazolium Dyes as Tools in Cell Biology: New Insights Into Their Cellular Reduction", Biotechnology Annual Review, pp. 127-141, vol. 11, 2005.
Buu-Hoi et al.,"2-Arylpyrrocolines and 2-Arylpyrimidazoles", Journal of Organic Chemistry, Sep. 9, 1953, pp. 1370-1375.
Craig, A.W.B. et al., "Mice Devoid of Fer Protein-Tyrosine Kinase Activity Are Viable and Fertile But Display Reduced Cortactin Phosphorylation", Molecular and Cellular Biology, Jan. 2001, pp. 603-613, vol. 21, No. 2.
Craig, A.W.B. et al., "Fer Kinase is Required for sustained p38 Kinase activation and Maximal Chemotaxis of Activated Mast Cells", Molecular and Cellular Biology, Sep. 2002, pp. 6363-6374, vol. 22, No. 18.
XP-002519065, Database WPI Week 199927, AN 1999-323456, Thomson Scientific, Apr. 27, 1999, pp. 1.
Greer, P.,"Closing in on the Biological Functions of FPS/FES and FER", Nat. Rev. Mol. Cell. Biol., Apr. 2002, pp. 278-289, vol. 3.
Hao, Q.L. et al., "Isolation And Sequence Analysis of a Novel Human Tyrosine Kinase Gene", Molecular and Cellular Biology, Apr. 1989, vol. 9, No. 4, pp. 1587-1593.
Khazi, I.M. et al., "Synthesis and Biological Activity of Some 3-methyl/ethoxycarbonyl-6-arylimidazo[2,1-b]thiazoles and their 5-bromo/5-formyl derivatives", Indian Journal of Chemistry, Feb. 2004, vol. 43B, pp. 393-398.
Kim, L. et al., "Growth Factor-dependent Phosphorylation of the Actin-binding Protein Cortactin Is Mediated by the Cytoplasmic Tyrosine Kinase FER", The Journal of Biological Chemistry, Sep. 4, 1998, vol. 273, No. 36, pp. 23542-23548.

(Continued)

Primary Examiner — Renee Claytor
Assistant Examiner — Sahar Javanmard
(74) Attorney, Agent, or Firm — Nath, Goldberg & Meyer; Sheldon M McGee; Lakshmi Rajan

(57) ABSTRACT

Provided is a pharmaceutical composition including as an active component a compound of formula (I):

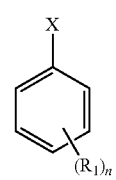

(I)

wherein X and $(R_1)_n$ are as defined, and a physiological acceptable carrier. Also provided is a method for treating cancer including administering to an individual in need of such treatment an effective amount of the presently described pharmaceutical composition.

5 Claims, 8 Drawing Sheets

OTHER PUBLICATIONS

Orlovsky, K., et al., "N-Terminal Sequences Direct the Autophosphorylation States of the FER Tyrosine Kinases in Vivo", Biochemistry, 2000, vol. 39, pp. 11084-11091.

Pasder, O. et al., "Downregulation of Fer induces PP1 activation and Cell-Cycle Arrest In Maglignant Cells", Oncogene, 2006, vol. 25, pp. 4194-4206.

Pasder, O. et al., "FER as a Novel Target for Cancer Therapy", Drugs of the Future, 2007, vol. 32, No. 1, pp. 61-70.

Penhallow, R.C. et al., "Temporal Activation of Nontransmembrane Protein-tyrosine, Kinases Following mast Cell FcERI Engagement", The Journal of Biological Chemistry, Oct. 6, 1995, vol. 270, No. 40, pp. 23362-23365.

Prevost, G.P. et al.; "Anticancer Activity of BIM-46174, a New Inhibitor of the Heterotrimeric $G\alpha/G\beta y$ Protein Complex", Canser Res. Sep. 15, 2006, vol. 66, No. 18, pp. 9227-9234.

International Search Report of PCT/IL2008/001099 mailed Mar. 26, 2009.

PHARMACEUTICAL COMPOSITIONS AND METHODS FOR THE TREATMENT OF CANCER

This is a National Phase Application filed under 35 U.S.C. 371 as a national stage of PCT/IL2008/001099, filed Aug. 10, 2008, an application claiming the benefit under 35 USC 119 (e) U.S. Provisional Application No. 60/935,364, filed Aug. 9, 2007, and U.S. Provisional Application No. 61/006,455, filed Jan. 15, 2008, the content of each of which is hereby incorporated by reference in its entirety.

FIELD OF THE INVENTION

This invention relates to pharmaceutical compositions and methods for the treatment of cancer.

BACKGROUND OF THE INVENTION

The following references are considered to be relevant for an understanding of the invention.

REFERENCES

Allard P, Zoubeidi A, Nguyen L T, Tessier S, Tanguay S, Chevrette M, Aprikian A and Chevalier S. (2000). *Mol. Cell. Endocrinol.,* 159, 63-77.
Berridge, M. V., Herst, P. M., and Tan, A. S. (2005). Tetrazolium dyes as tools in cell biology: new insights into their cellular reduction. Biotechnol. Annu. Rev. 11, 127-152]
Craig A W and Greer P A. (2002). *Mol. Cell. Biol.,* 22, 6363-6374.
Craig A W, Zirngibl R, Williams K, Cole L A and Greer P A. (2001). *Mol. Cell. Biol.,* 21, 603-613.
Greer P. (2002). *Nat. Rev. Mol. Cell. Biol.,* 3, 278-289.
Hao Q-L, Heisterkamp N and Groffen J. (1989). *Mol. Cell. Biol.,* 9, 1587-1593.
Kim L and Wong T W. (1998). *J. Biol. Chem.,* 273, 23542-23548.
Orlovsky K, Ben-Dor I, Priel-Halachmi S, Malovany H and Nir U. (2000). *Biochemistry,* 39, 11084-11091.
Penhallow R C, Class K, Sonoda H, Bolen J B and Rowley R B. (1995). *J. Biol. Chem.,* 270, 23362-23365.
Pasder, O., Shpungin, S., Salem, Y., Makovsky, A., Vilchick, S., Michaeli, S., Malovani, H. and Nir, U. (2006) *Oncogene,* 25, 4194-4206.
Pasder, O., Salem, Y., Yaffe, E., Shpungin, S, and Nir, U. (2007) *Drugs of the Future,* 32, 61-70.

Fer is an intracellular tyrosine kinase that resides in both the cytoplasm and nucleus of mammalian cells and is activated by growth factors such as EGF and PDGF in fibroblastic cells (Kim and Wong, 1998), and by occupation of the Fcγ receptor in mast cells (Penhallow et al., 1995). Although present in a wide variety of tissues and cells, the functional role of Fer has been elucidated mainly in cells which carry out innate immune responses (Craig and Greer, 2002; Greer, 2002). Mice devoid of an active Fer develop normally and the proliferation of fibroblasts derived from these mice is not impaired in vitro (Craig et al., 2001).

Fer has been detected in all human malignant cell lines analyzed (Hao et al., 1989; Orlovsky et al., 2000) and its levels in malignant prostate tumors are significantly higher then those detected in benign prostate tumors (Allard et al., 2000). Furthermore, down-regulation of Fer impaired the proliferation of prostate and breast carcinoma cells (Pasder et al., 2006) and abolished the ability of prostate carcinoma PC3 cells to form colonies in soft agar (Allard et al., 2000). U.S. patent application Ser. No. 10/486,101 having Publication Number 20050063973 discloses short interfering RNA (siRNA) molecules directed to sequences of the fer gene. These siRNA molecules were found to inhibit the growth of PC3 cells and to arrest tumor growth in an animal model (Pasder et al., 2007).

SUMMARY OF THE INVENTION

In its first aspect, the present invention provides pharmaceutical compositions. A pharmaceutical composition according to the invention comprises as an active component a compound of formula (I):

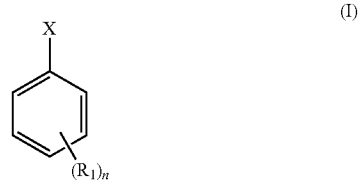

(I)

X is selected from the following:

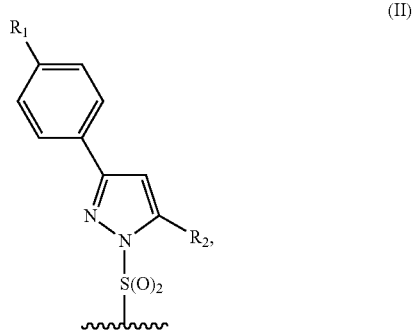

(II)

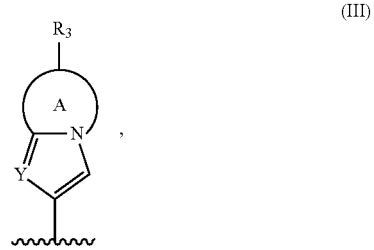

(III)

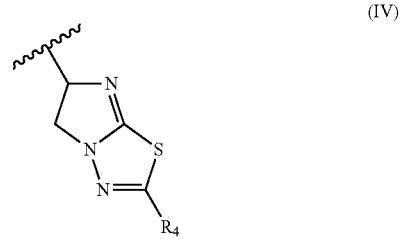

(IV)

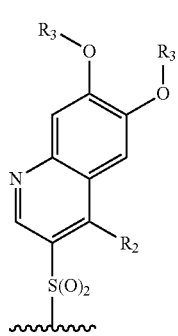

(V)

wherein $R_1$ is independently selected from H, F, Cl, Br, I or a $C_{1-5}$ linear or branched alkyl; n is 1, 2, 3, 4 or 5; $R_2$ is $N(R)_2$, R being independently hydrogen or linear or branched $C_{1-5}$alkyl group; $R_3$ is a linear or branched $C_{1-5}$alkyl group; $R_4$ is a group of formula

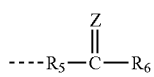

$R_5$ being a 5- or 6-membered aromatic or non-aromatic ring optionally having one, two or three heteroatoms selected from O, N or S; $R_6$ being a 5- or 6-membered aromatic or non-aromatic ring optionally having one, two or three heteroatoms selected from O, N or S optionally having one or two substituents independently selected from halogen and a linear or branched $C_{1-5}$alkyl group; Z is selected from O or S; Y is C—H or N; and A is a 5- or 6-membered fused aromatic or non aromatic ring optionally being a heterocyclic ring comprising 1 to 3 heteroatoms selected from O, N or S; and a physiological acceptable carrier.

$C_{1-5}$ Linear or branched alkyl means a methyl, ethyl, propyl, isopropyl, n-butyl, isobutyl, sec.-butyl, tert.-butyl, n-pentane, iso-pentane, sec.-pentane or tert.-pentane that may optionally be partially substituted by halogen selected from F, Cl, Br, or I.

The invention is directed to a pharmaceutical composition comprising as an active ingredient a compound of formula (I) as defined above, where $R_1$ is H, F, Cl, $CH_3$, $C_2H_5$ or $C_3H_7$; n is 1, 2 or 3; X is a compound selected from formulae (II) to (VI); $R_2$ is $N(R)_2$, R being independently hydrogen or $CH_3$, $C_2H_5$ or $C_3H_7$; $R_3$ is a linear or branched $C_{1-5}$alkyl group; $R_4$ is a group of formula:

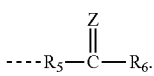

$R_5$ being a 5- or 6-membered aromatic or non-aromatic ring optionally having one, two or three heteroatoms selected from O, N or S; $R_6$ being a 5- or 6-membered aromatic or non-aromatic ring optionally having one, two or three heteroatoms selected from O, N or S optionally having one or two substituents independently selected from halogen and a linear or branched $C_{1-5}$alkyl group; Z is selected from O or S; Y is C—H or N; and A is a 5- or 6-membered fused aromatic or non aromatic ring optionally being a heterocyclic ring comprising 1 to 3 heteroatoms selected from O, N or S.

In particular, the pharmaceutical compositions of the invention have been found to inhibit the growth of cancer cells. Without wishing to be bound by a particular theory, it is believed that the pharmaceutical compositions of the invention inhibit the expression or the activity of Fer in the treated cells.

In one preferred embodiment, the pharmaceutical composition of the invention comprises a compound, referred to herein as "compound 497", having chemical formula $C_{15}H_7ClF_5N_3O_2S$ and (VI):

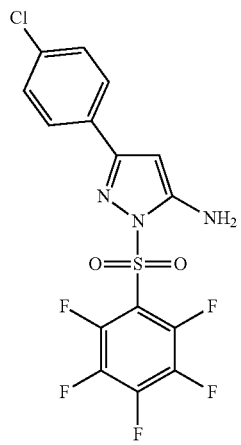 [SMILES: Nc1cc(-c2ccc(Cl)cc2)nn1S(=O)(=O)c1c(F)c(F)c(F)c(F)c1F]

In another preferred embodiment, the pharmaceutical composition of the invention comprises a compound, referred to herein as "compound 631", having the chemical formula $C_{13}H_{12}FN_3S$ and (VII):

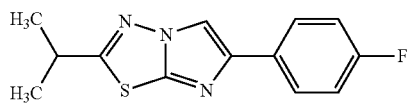

In yet another preferred embodiment, the pharmaceutical composition of the invention comprises a compound, referred to herein as "compound 115", having the chemical formula $C_{15}H_{12}FN$ and (XIII):

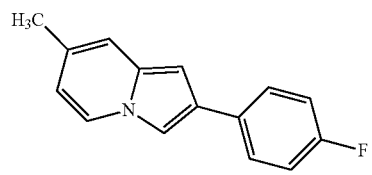 [SMILES: Cc1ccn2cc(-c3ccc(F)cc3)cc2c1]

In yet another preferred embodiment, the pharmaceutical composition of the invention comprises a compound, referred to herein as "compound 540", having the chemical formula $C_{21}H_{24}N_2O_4S$ and (IX):

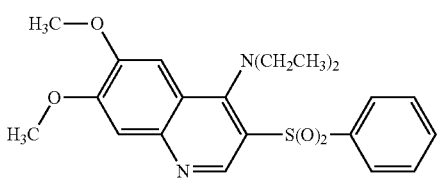

In still another preferred embodiment, the pharmaceutical composition of the invention comprises a compound, referred to herein as "compound E626-0342", having the chemical formula $C_{22}H_{28}N_6OS$ (X):

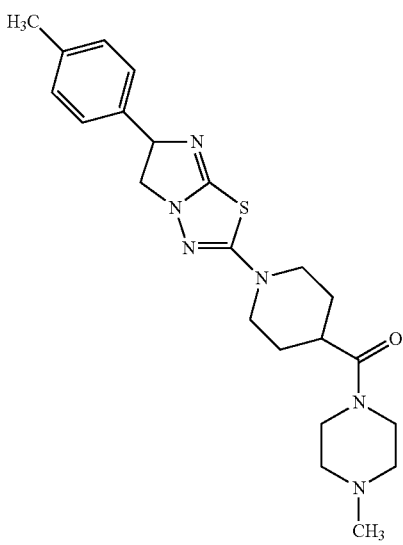 [SMILES: Cc1ccc(C2CN3N=C(N4CCC(C(=O)N5CCN(C)CC5)CC4)SC3=N2)cc1]

In its second aspect, the invention provides a method for treating cancer. In accordance with this aspect of the invention, an individual in need of such treatment is administered an effective amount of a pharmaceutical composition of the invention.

The invention further provides use of a compound of formula (I):

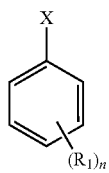
(I)

X is selected from the following:

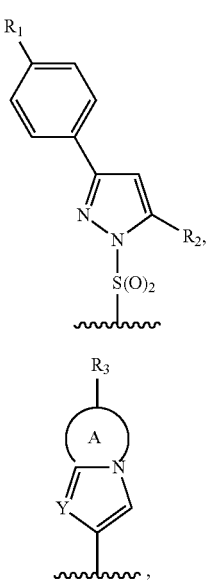

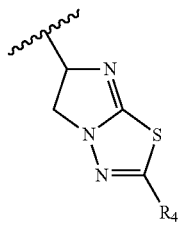
(IV)

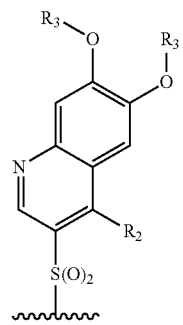
(V)

wherein $R_1$ is independently selected from H, F, Cl, Br, I or a $C_{1-5}$ linear or branched alkyl; n is 1, 2, 3, 4 or 5; $R_2$ is $N(R)_2$, R being independently hydrogen or linear or branched $C_{1-5}$alkyl group; $R_3$ is a linear or branched $C_{1-5}$alkyl group; $R_4$ is a group of formula

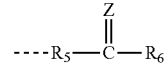

$R_5$ being a 5- or 6-membered aromatic or non-aromatic ring optionally having one, two or three heteroatoms selected from O, N or S; $R_6$ being a 5- or 6-membered aromatic or non-aromatic ring optionally having one, two or three heteroatoms selected from O, N or S optionally having one or two substituents independently selected from halogen and a linear or branched $C_{1-5}$alkyl group; Z is selected from O or S; Y is C—H or N; and A is a 5- or 6-membered fused aromatic or non aromatic ring optionally being a heterocyclic ring comprising 1 to 3 heteroatoms selected from O, N or S; for the preparation of a medicament for the treatment of cancer.

BRIEF DESCRIPTION OF THE DRAWINGS

In order to understand the invention and to see how it may be carried out in practice, embodiments will now be described, by way of non-limiting example only, with reference to the accompanying drawings, in which.

EXAMPLES

Compounds 497, 631, 115 and 540

The effect of the four compounds 497, 631, 115 and 540 on the growth profile of cancer cells which express Fer was tested. The cells that were tested were: the colon cancer cell lines HT29 and HCT 116, the breast cancer cell lines MDA-MB-231 and MCF-7, and the prostate cancer cell lines PC3 and DU145. The effect of each of the four compounds on FS11 cells, a non malignant fibroblastic cell line, was also studied.

The cells were seeded in 96 wells microplates and were left to grow untreated overnight. Each of the three compounds was dissolved in DMSO and was then added to each well in a dose dependent manner from 0.4 to 80 µM. The concentration of DMSO in each well was 0.4% v/v. Untreated cells and cells subjected to 0.4% DMSO alone, served as controls. The number of viable cells in each well was determined 48, 72, 96 hours after compounds addition, using the XTT test (Berridge, M. V. et al, 2005). In cases where complete inhibition of cell growth was observed in the presence of one of the three compounds tested at one of the concentrations tested, the IC50 of the compound on that cell line was determined.

Figure 1:
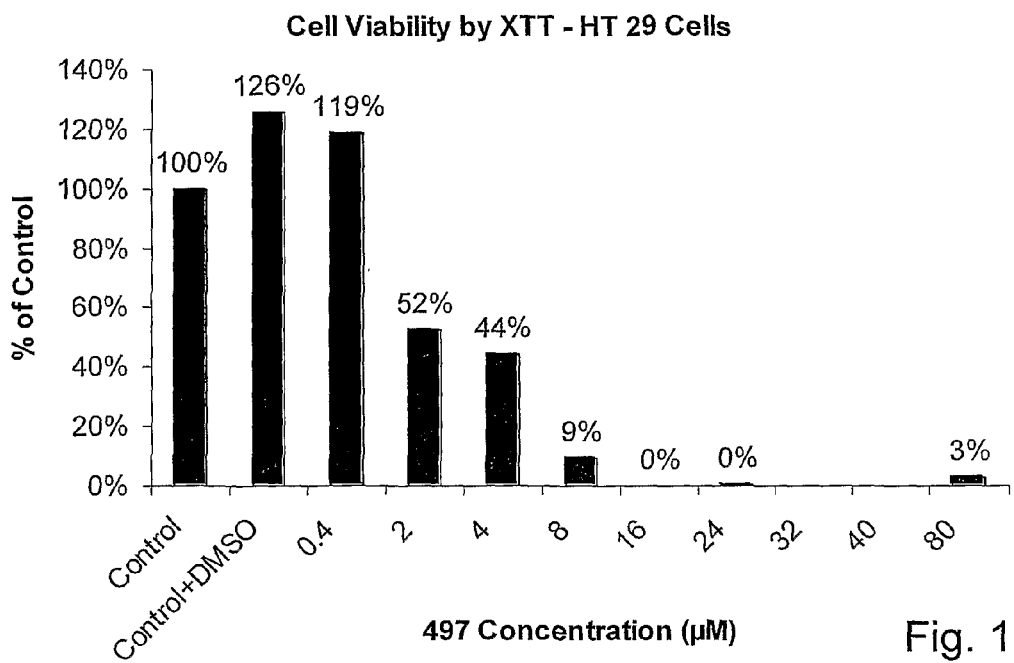
FIG. 1 shows the effect of compound 497 on HT29 human colorectal carcinoma cells.
Figure 2:
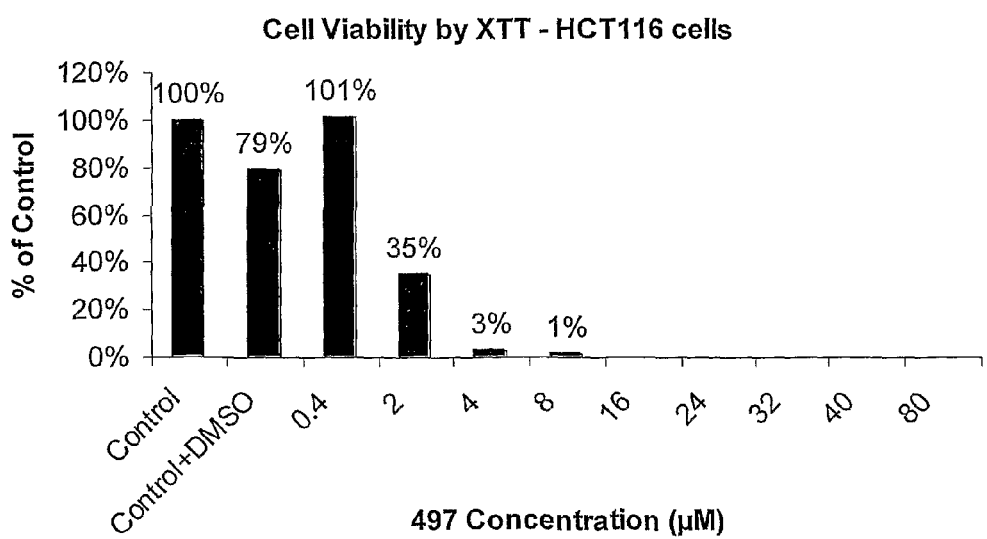
FIG. 2 shows the effect of compound 497 on HCT116 human colorectal carcinoma cells.
Figure 3:
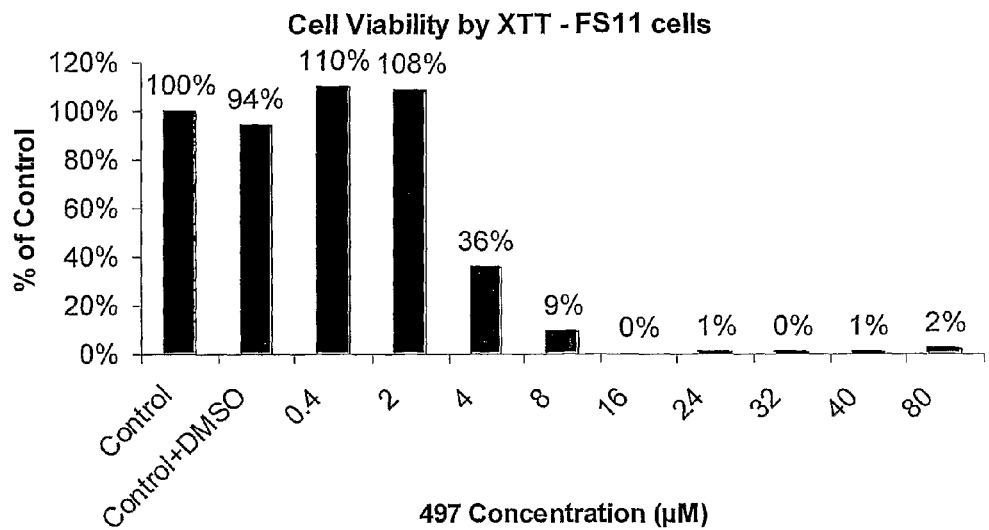
FIG. 3 shows the effect of compound 497 on FS 11 human fibroblastic cells.

FIGS. 1 and 2 show the effect of compound 497 on the growth of the colorectal cancer cell lines HT29 and HCT116, respectively. In FIGS. 1 and 2, it can be seen that compound 497 caused a profound reduction in the number of viable cells in both cell lines of treated cultures with an IC50 of 2 µM for HT29 and HCT116 after 96 h. FIG. 3 shows the effect of compound 497 on the non-malignant FS 11 cell line.

Figure 4:
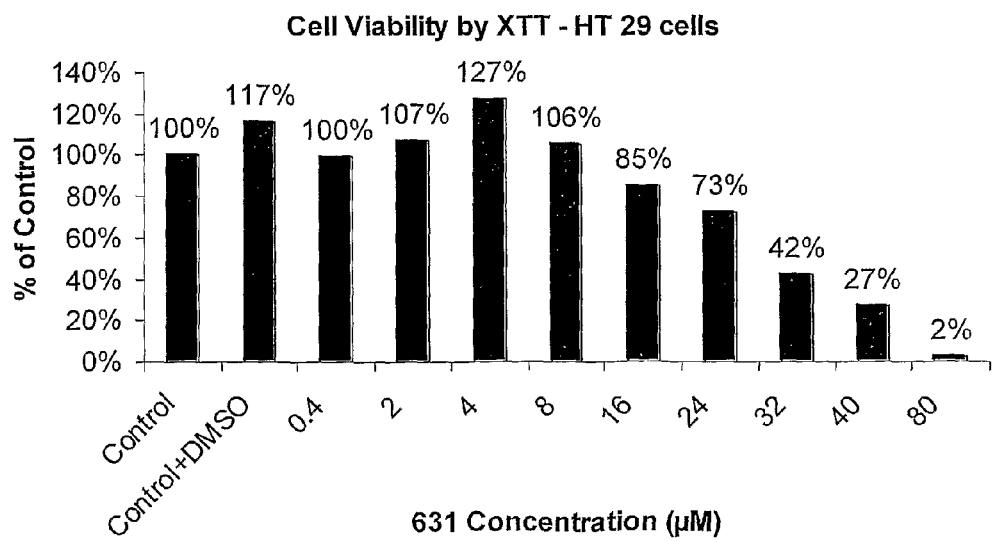
FIG. 4 shows the effect of compound 631 on HT29 colorectal carcinoma cells.
Figure 5:
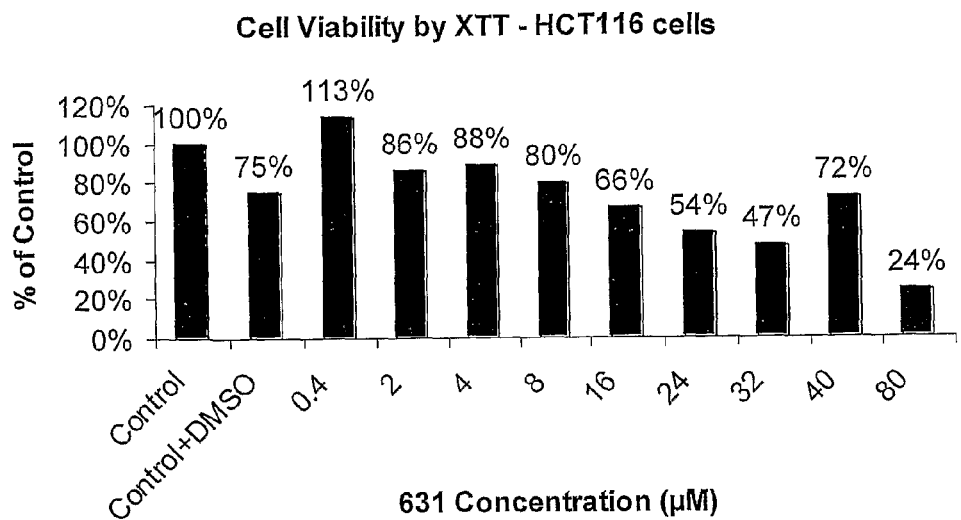
FIG. 5 shows the effect of compound 631 on HcT116 colorectal carcinoma cells.
Figure 6:
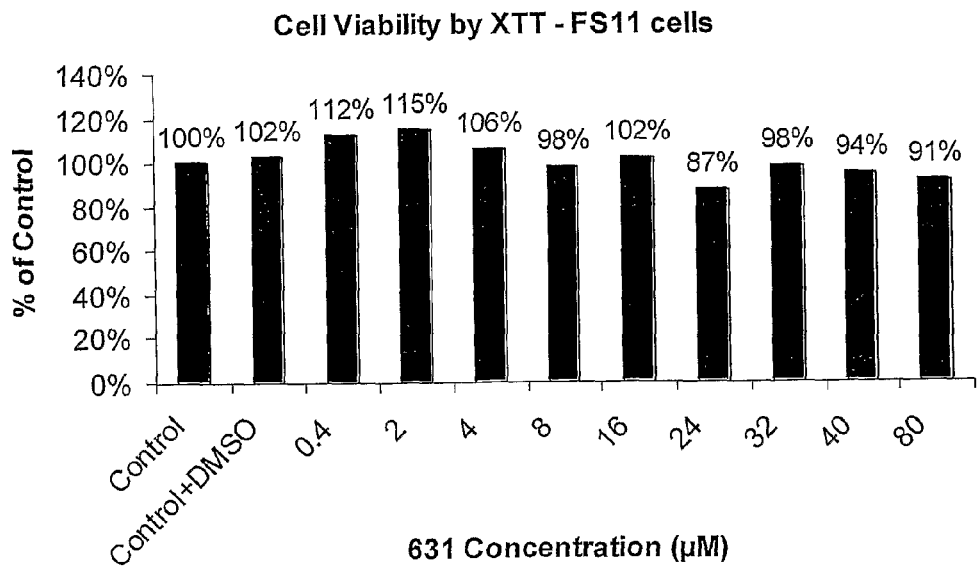
FIG. 6 shows the effect of compound 631 on FS 11 human fibroblastic cells.
Figure 7:
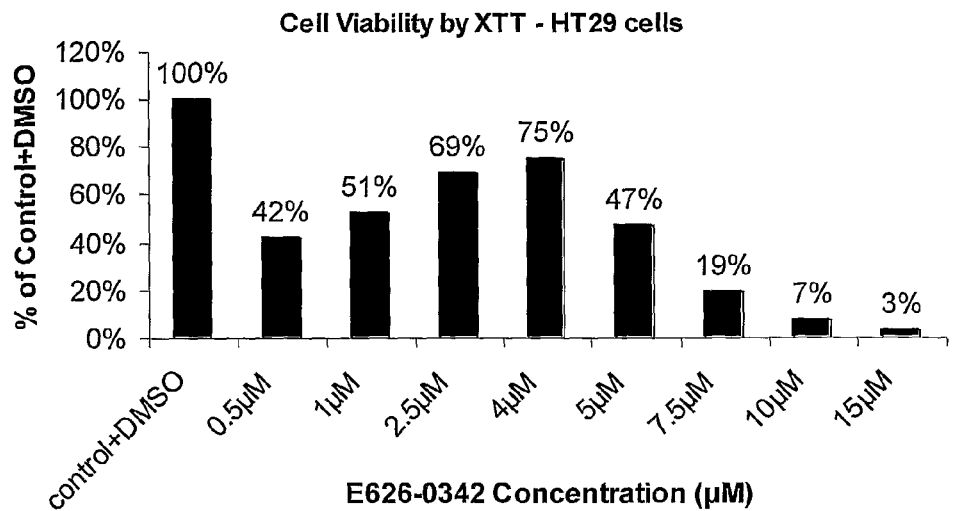
FIG. 7 shows the effect of the compound E626-0342 on HT29 human colon carcinoma cells.
Figure 8:
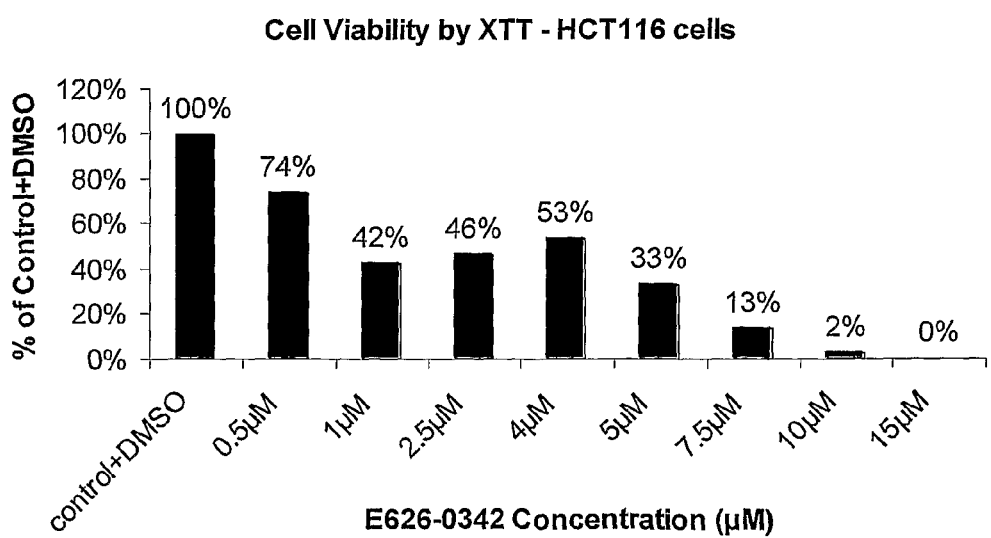
FIG. 8 shows the effect of compound E626-0342 on HCT116 human colon carcinoma cells.

FIGS. 4 and 5 show the effect of compound 631 on the growth of the colorectal cancer cell lines HT29 and HCT116, respectively. FIG. 6 shows the effect of compound 631 on the non-malignant FS 11 cell line. Compound 631 also caused a decrease in cell viability with an EC50 of 40 µM for HT29 and 24 µM for HCT116 (FIGS. 7, 8). Compound 631 did not affect FS11 cells up to a concentration of 80 µM (FIG. 6).

Table 1 shows the EC50 in µM of the four compounds on the various cell lines examined for those cases where an EC50 could be determined from the concentrations of the compounds that were tested (up to 80 µM).

TABLE 1

| Cell Line | Compound 497 | Compound 631 | Compound 115 | Compound 540 |
|---|---|---|---|---|
| HT29 | 2 | 30 | 32 | 40 |
| HCT116 | 2 | 24 | 32 | 40 |
| MDA-MB-231 | 2 | 32 | 40 | 25 |
| MCF-7 | 8 | | 8 | 25 |
| PC3 | 4 | 32 | | 15 |

TABLE 1-continued

| Cell Line | Compound 497 | Compound 631 | Compound 115 | Compound 540 |
|---|---|---|---|---|
| DU145 | 8 | | | 20 |
| FS11 | 4 | | >80 | 40 |

To examine whether the above listed compounds affect the enzymatic activity of Fer, the protein tyrosine phosphorylation profile in yeast cells which ectopically express the murine Fer, was analyzed using the yeast system disclosed in WO2007/107991. Since the *S. cerevisae* yeast cells lack almost completely detectable, endogenous, tyrosine phosphorylation activity, the detected tyrosine phosphorylation signals result essentially from the kinase activity of the ectopic Fer. Furthermore, considering the negligible tyrosine-phosphorylation background in the cells, it is possible to specifically track the tyrosine phosphorylation level of Fer in the treated yeast cells.

Figure 12:
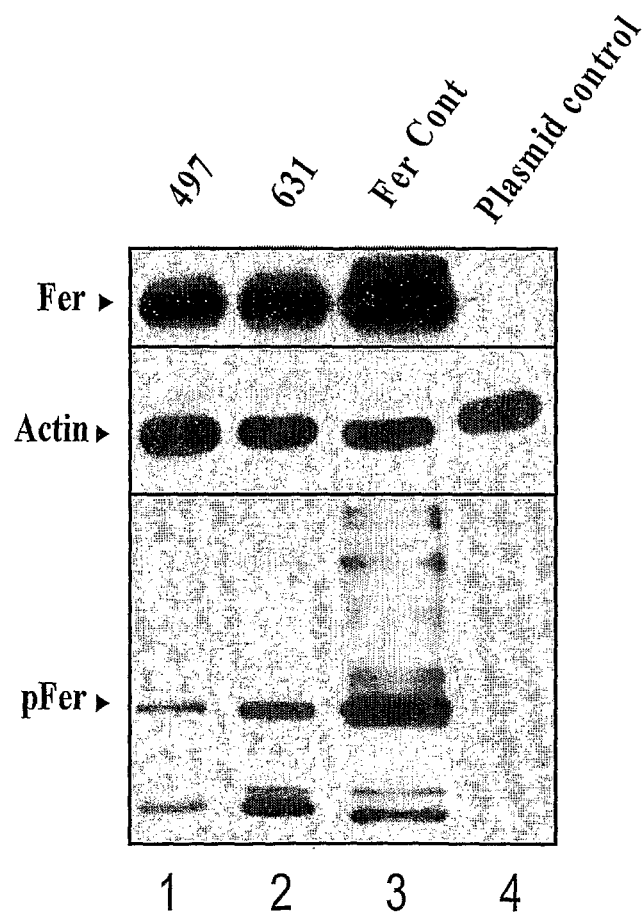
FIG. 12 shows inhibition of the kinase activity of Fer in yeast cells by compounds 497 and 631.

Yeast cells expressing an ectopic Fer were treated with 40 µM of one of the compounds 497, 631, 115 and 540 for 48 h. Whole cell lysates were then prepared and resolved in SDS-poly acrylamide gel. The expression levels of Fer and the tyrosine phosphorylation profiles of the proteins before and after treatment with the compounds were determined using a western-blot analysis. FIG. 12 shows a Western Blot in which lane 4 of shows yeast cells containing the empty expression vector-pAES, lane 3 shows yeast cells harboring the plasmid pAES-Fer and expressing an ectopic Fer, lane 2 shows cells harboring pAES-Fer, expressing Fer and treated with compound 631 and lane 1 shows cells harboring pAES-Fer, expressing Fer and treated with compound 497. The lower panel shows—membrane reacted with anti-phosphotyrosine antibody. The arrow indicates the tyrosine phosphorylated Fer (pFer). The upper panel shows membrane reacted with an anti-Fer antibody, thus representing the level of the Fer protein. The middle panel shows the level of the house-keeping protein actin, which served as a control for protein loading quantities. This revealed a significant reduction in the tyrosine phosphorylation level of the 94 id) band which represents the Fer protein, in cells treated with compounds 631 and 497 (FIG. 12). Thus, the compounds 631 and 497, significantly inhibit the Fer kinase autophosphorylation enzymatic activity.

Compound E626-0342

The effect of compound E626-0342 on the growth profile of cancer cells which express Fer was tested. The compound was added to the growth media of FS11-normal primary human fibroblasts and to two colon cancer cell lines, HCT116 and HT29, which express Fer.

Various cell lines were seeded in 96 wells microplates and were left to grow untreated overnight. Compound E626-0342, dissolved in DMSO at a stock concentration of 10 mM was then added to each well in a dose dependent manner, resulting in final concentrations extending from 0.5 to 15 µM. The final concentration of DMSO in each well was 1% v/v. Untreated cells and cells subjected to 1% DMSO alone, served as controls. The number of viable cells in each well was determined 96 hours after addition of the compound, using the XTT test (Berridge, M. V. et al, 2005).

In FIGS. 7 and 8, it can be seen that compound E626-0342 caused a profound reduction in the number of viable cells in the two colon cancer cell lines, to which it was added. The compound exhibited an $EC_{50}$ of 1 μM for both HT29 and HCT116, after 96 h of treatment. At a concentration of 10 μM, less then 10% of viable cells were left in each of the two treated colon cell lines.

Figure 9:
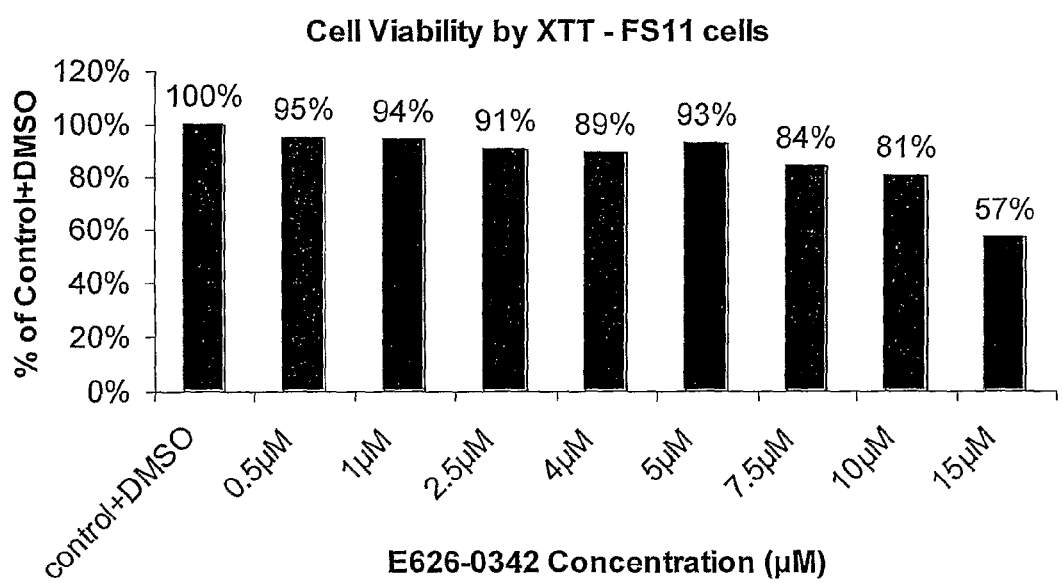
FIG. 9 shows the effect of compound E626-0342 on FS 11 normal human fibroblasts.

Notably, E626-0342 did not affect normal human FS11 fibroblasts, up to a concentration of 10 μM (FIG. 9).

To examine whether E626-0342 affects the enzymatic activity of Fer, the protein tyrosine phosphorylation profile in yeast cells which ectopically express the murine Fer, was analyzed. Since the *S. cerevisae* yeast cells lack almost completely detectable, endogenous, tyrosine phosphorylation activity, the detected tyrosine phosphorylation signals result essentially from the kinase activity of the ectopic Fer. Furthermore, considering the negligible tyrosine-phosphorylation background in the cells, it is possible to specifically track the tyrosine phosphorylation level of Fer in the treated yeast cells.

Figure 10:
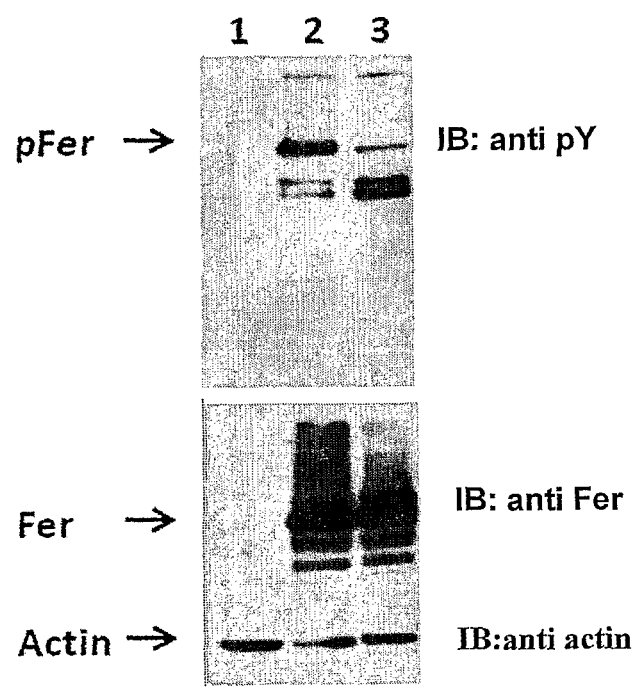
FIG. 10 shows inhibition of tyrosine kinase Fer activity by E626-0342.

Yeast cells expressing an ectopic Fer were treated with 40 μM E626-0342 compound for 48 h. Whole cell lysates were then prepared and resolved in SDS-poly acrylamide gel. The expression levels of Fer and the tyrosine phosphorylation profile of the proteins before and after treatment with the compound were determined using a western-blot analysis. This revealed a significant reduction in the tyrosine phosphorylation level of a 94 kD band which represents the Fer protein (FIG. 10). Thus, the E626-0342 compound significantly inhibits the Fer kinase autophosphorylation enzymatic activity.

Referring now to FIG. 10 a Western Blot is shown. Lane 1 shows yeast cells containing the empty expression vector-pAES, lane 2 shows yeast cells harboring the plasmid pAES-Fer and expressing an ectopic Fer, and lane 3 shows cells harboring pAES-Fer, expressing Fer and treated with E626-0342. The upper panel shows—membrane reacted with anti-phosphotyrosine antibody. Arrow indicates the tyrosine phosphorylated Fer (pFer). The lower panel shows membrane reacted with an anti-Fer antibody and anti-actin antibody, which served as a control for protein loading quantities. The upper arrow indicates the Fer protein, the lower arrow indicates actin.

As seen in FIG. 10, compound E626-0342 exhibited a significant dose dependent growth restoring effect on the HA-Fer expressing yeasts cells. This indicated an effect of this compound on the functioning of the tyrosine kinase Fer. This compound was not toxic to yeast cells in concentrations up to 40 μM.

Figure 11:
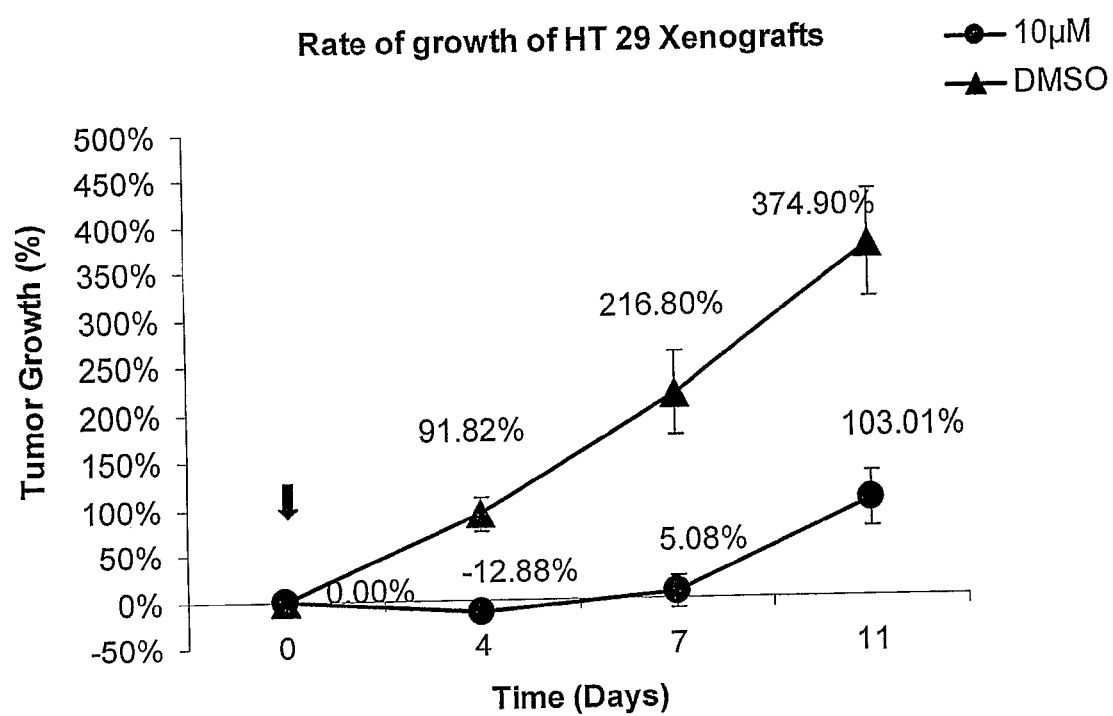
FIG. 11 shows the effect of E626-0342 on the progression of Ht29 xenografts in "nude" mice.

To test the effect of the E626-0342 compound on tumor progression in-vivo, $1 \times 10^6$ HT29 colon carcinoma cells were injected subcutaneously to immuno-compromised "nude" mice. Xenografts were allowed to develop for 7 days in each mouse, and then 50 μl of 10 μm E626-0342 dissolved in 2% DMSO in Hank's Balanced Salt Solution (HBSS) buffer (CaCl2—0.14 g/l, KCl—0.4 g/l, KH2PO4—0.06 g/l, MgCl2*6H2O—0.1 g/l, MgSO4*7H2O—0.1 g/l, NaCl—8 g/l, NaHCO3—0.35 g/l, Na2HPO4*7H2O—0.09 g/l and D-Glucose—1 g/l) were injected every other day into the tumor of each of 12 mice. A 2% DMSO solution in HBSS was injected to the tumor of each of 15 mice that served as a control group. Tumor sizes were measured twice a week and the differences in the size of each tumor were determined. The average difference in tumor size in each of the two groups was plotted after determining standard error. In FIG. 11 it can be seen that E626-0342 significantly attenuated the progression of the HT29 xenografts.

The invention claimed is:

1. A pharmaceutical composition comprising as an active component a compound of formula (I):

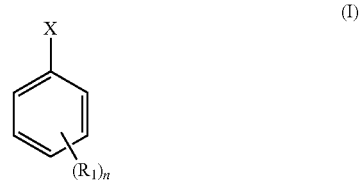

X is selected from the following:

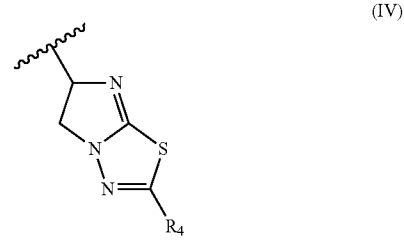

wherein $R_1$ is independently selected from H, F, Cl, Br, I or a $C_{1-5}$ linear or branched alkyl; n is 1, 2, 3, 4 or 5; $R_4$ is a group of formula

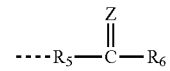

$R_5$ being a 5- or 6-membered aromatic or non-aromatic ring optionally having one, two or three heteroatoms selected from O, N or S; $R_6$ being a 5- or 6-membered aromatic or non-aromatic ring optionally having one, two or three heteroatoms selected from O, N or S optionally having one or two substituents independently selected from halogen and a linear or branched $C_{1-5}$ alkyl group; Z is selected from O or S;

and a physiological acceptable carrier.

2. The pharmaceutical composition according to claim 1, wherein $R_1$ is H, F, Cl, CH₃, C₂H₅ or C₃H₇; n is 1, 2 or 3; X is a compound selected from formula IV; $R_4$ is a group of formula:

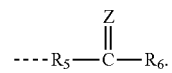

$R_5$ being a 5- or 6-membered aromatic or non-aromatic ring optionally having one, two or three heteroatoms selected from O, N or S; $R_6$ being a 5- or 6-membered aromatic or non-aromatic ring optionally having one, two or three heteroatoms selected from O, N or S optionally having one or two substituents independently selected from halogen and a linear or branched $C_{1-5}$ alkyl group; Z is selected from O or S;

and a physiological acceptable carrier.

3. The pharmaceutical composition according to claim 1, wherein the compound is:

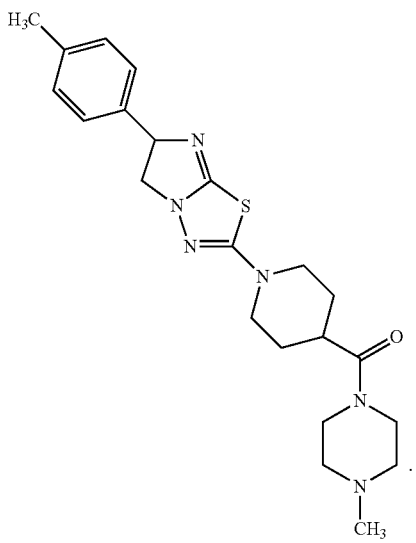 [SMILES: Cc1ccc(C2CN3N=C(N4CCC(C(=O)N5CCN(C)CC5)CC4)SC3=N2)cc1]

4. A method for treating: cancer, comprising administering to an individual in need thereof a therapeutically effective amount of a pharmaceutical composition comprising as an active component a compound of formula (I):

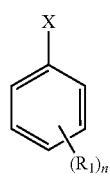

(I)

X is selected from the following:

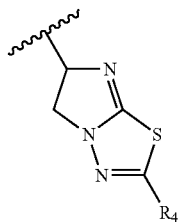

(IV)

wherein $R_1$ is independently selected from H, F, Cl, Br, I or a $C_{1-5}$ linear or branched alkyl; n is 1, 2, 3, 4 or 5; $R_4$ is a group of formula

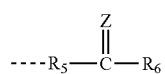

$R_5$ being a 5- or 6-membered aromatic or non-aromatic ring optionally having one, two or three heteroatoms selected from O, N or S; $R_6$ being a 5- or 6-membered aromatic or non-aromatic ring optionally having one, two or three heteroatoms selected from O, N or S optionally having one or two substituents independently selected from halogen and a linear or branched $C_{1-5}$ alkyl group; Z is selected from O or S.

5. A method for treating: cancer comprising administering to an individual in need of such treatment an effective amount of a pharmaceutical composition according to claim 1.

* * * * *

UNITED STATES PATENT AND TRADEMARK OFFICE
CERTIFICATE OF CORRECTION

PATENT NO. : 8,481,572 B2
APPLICATION NO. : 12/672157
DATED : July 9, 2013
INVENTOR(S) : Uri Nir et al.

It is certified that error appears in the above-identified patent and that said Letters Patent is hereby corrected as shown below:

In the Claims

- Claim 4, Column 11, Line 25: after "treating" and before "cancer",
  Please delete ":" and replace with --colon--

- Claim 5, Column 12, Line 33: after "treating" and before "cancer",
  Please delete ":" and replace with --colon--

Signed and Sealed this
First Day of October, 2013

Teresa Stanek Rea
*Deputy Director of the United States Patent and Trademark Office*